United States Patent [19]
LeMay

[11] 3,973,128
[45] Aug. 3, 1976

[54] TOMOGRAPHY

[75] Inventor: Christopher Archibald Gordon LeMay, Osterley, England

[73] Assignee: EMI Limited, Mayes, England

[22] Filed: July 31, 1974

[21] Appl. No.: 493,403

[30] Foreign Application Priority Data
Aug. 18, 1973 United Kingdom............... 39145/73

[52] U.S. Cl. .............................. 250/445 T; 250/320
[51] Int. Cl.[2].......................................... G01N 23/00
[58] Field of Search ................ 250/445 T, 320, 523, 250/524, 525

[56] References Cited
UNITED STATES PATENTS

| | | | |
|---|---|---|---|
| 3,281,598 | 10/1966 | Hollstein............................ | 250/525 |
| 3,484,604 | 12/1969 | Matsuda et al.................. | 250/445 T |
| 3,499,146 | 3/1970 | Richards.......................... | 250/445 T |
| 3,670,163 | 6/1972 | Lajus................................ | 250/320 |
| 3,684,886 | 8/1972 | Muehllegner .................... | 250/445 T |
| 3,714,429 | 1/1973 | McAfee et al. ................. | 250/445 T |
| 3,742,236 | 6/1973 | Richards.......................... | 250/445 T |
| 3,818,220 | 6/1974 | Richards.......................... | 250/445 T |
| 3,852,611 | 12/1974 | Cesar ............................... | 250/445 T |

Primary Examiner—Alfred E. Smith
Assistant Examiner—B. C. Anderson
Attorney, Agent, or Firm—Fleit & Jacobson

[57] ABSTRACT

For examining a body by means of X-rays or other penetrating radiation, data is determined representing the absorption suffered by each of a plurality of beams which are passed through the body. The beams are effectively arranged in a plurality of sets of beams, in a single plane, at many different angles. The arrangement is such that the amount of information provided by the beams is a function, which is in part non-uniform, of the beam position in the set. A reconstruction of the distribution of absorption of the radiation within a part of the body is derived from the absorption data so determined.

13 Claims, 10 Drawing Figures

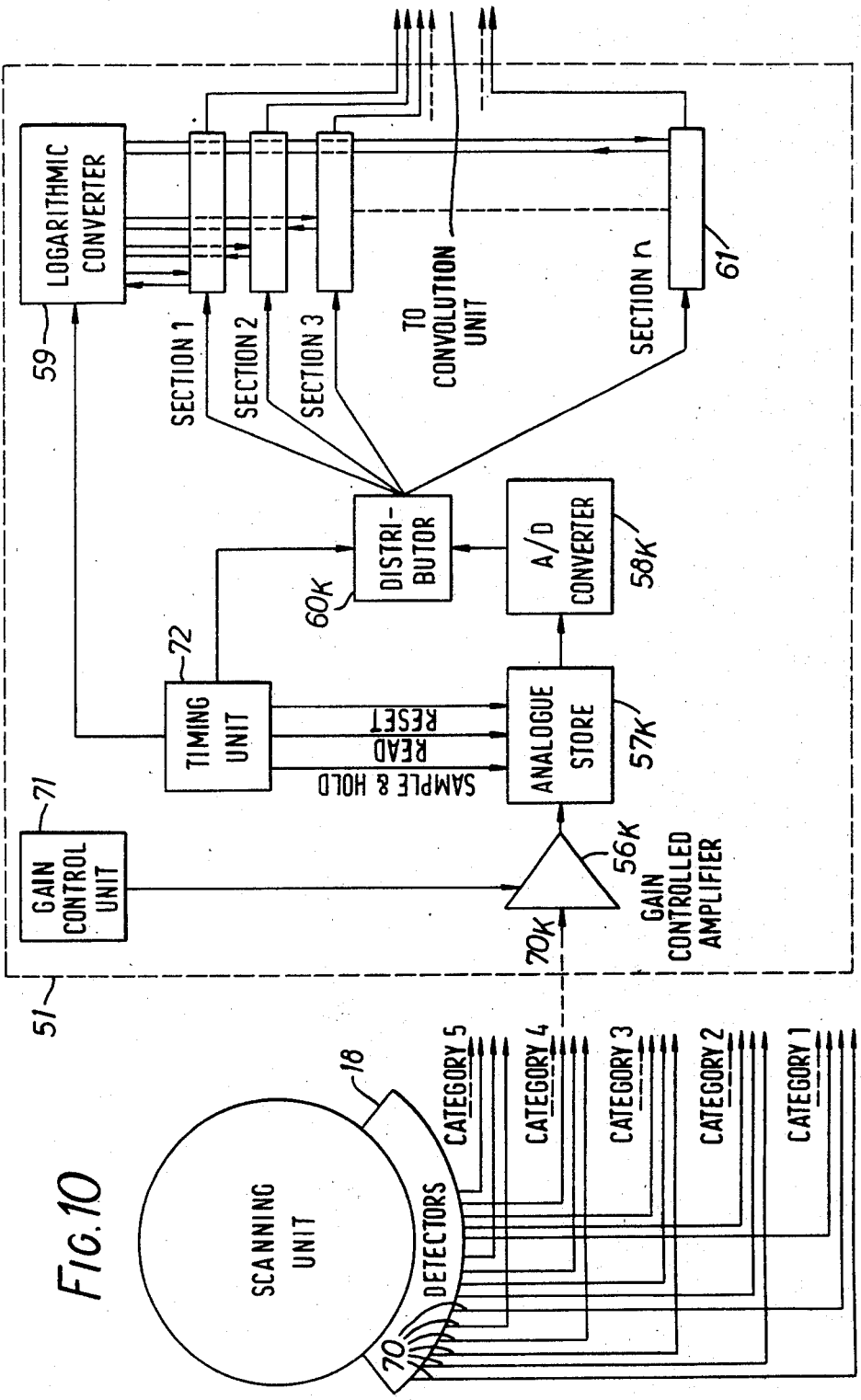

TOMOGRAPHY

This invention relates to a method of and apparatus for examining a body by means of radiation such as X or γ radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

In the method of, and apparatus, for examining a body described and claimed in British Patent Specification No. 1,283,915 radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about an axis normal to the plane. The various dispositions thus lie in a plane through the body over which the distribution of absorption coefficient, for the radiation used, is derived by processing the beam absorption data provided by the detector. The processing is such that the finally displayed distribution of absorption is the result of successive approximations.

The method and apparatus described in the aforesaid British Patent has proved to be successful for producing cross-sectional representation of parts of the living body, such as the head.

In our co-pending U.S. patent application Ser. No. 462,104 filed Apr. 18, 1974 now U.S. Pat. No. 3,924,129 there is described a further method and apparatus having a method of data acquisition essentially the same as that referred to in regard to the aforesaid British Patent Specification while the method of processing of the data is more flexible and differs for the reason that it is based upon a convolution technique.

One advantage of employing a convolution technique to derive an image of the absorption distribution in the exploring plane is that, unlike the iterative method of reconstruction described in the aforesaid British Patent Specification, it is not necessary to reconstruct the whole of the absorption pattern in the exploring plane in order simply to reconstruct a part, rather if a special locality alone is of interest this region only may be made the subject of reconstruction, with economy, for instance, in time of reconstruction. The ability to reconstruct the absorption pattern over a limited area of interest is of particular value in the examination of parts of a body of large cross-sectional area as in the example of the human torso.

It is undesirable however on grounds of economy of equipment, given that the area over which it is required to examine closely will not normally amount to more than a minor fraction of the total cross-sectional area, for the apparatus to operate with the ability to resolve the pattern over the total area in fine detail. Following out the technique described in said Cognated Application, however, the apparatus would be subject to this objection.

An object of the present invention is to overcome this difficulty.

According to the invention there is provided apparatus for examining a body by means of penetrating radiation, such as X- or γ- radiation comprising a radiation source projecting radiation in a plane, a plurality of detectors in said plane spaced from said source to provide space for locating the body between the source and detectors so that a plane section of the body is irradiated by said radiation, the lateral extent of the radiation being sufficient to irradiate a substantial area of said plane section, said plurality of detectors including collimators and being laterally spaced to detect radiation along different beams within the lateral extent of said radiation, a rotatable support on which the source and detectors are mounted to rotate, around the body, about a common axis normal to the said plane and the lateral spacing of the centrelines of the beams being non uniform.

According to a further aspect of the invention there is provided a method of examining a selected area of a planar section of a body by means of penetrating radiation, such as X- or γ- radiation, including the steps of,
a. projecting the radiation in the plane of the said section,
b. determining the absorption suffered by the radiation after passage through the body, along a plurality of beams lying in the said plane, and
c. repeating the said determination of absorption for further pluralities of such beams at different angular positions in the said plane, in which the centrelines of beams passing through the said selected area are arranged to be relatively more closely spaced than the centrelines of beams, which do not pass through the selected area and the determinations of absorption for the said beams not passing through the selected area are used to correct for the effects on the beams passing through the selected area of absorption of radiation by the remaining parts of the said section.

In order that the invention may be clearly understood and readily carried into effect one example thereof will now be described with reference to the accompanying drawings of which:

FIG. 10 illustrates means for deriving absorption data in a form suitable in particular to the special processing.

Figure 1:
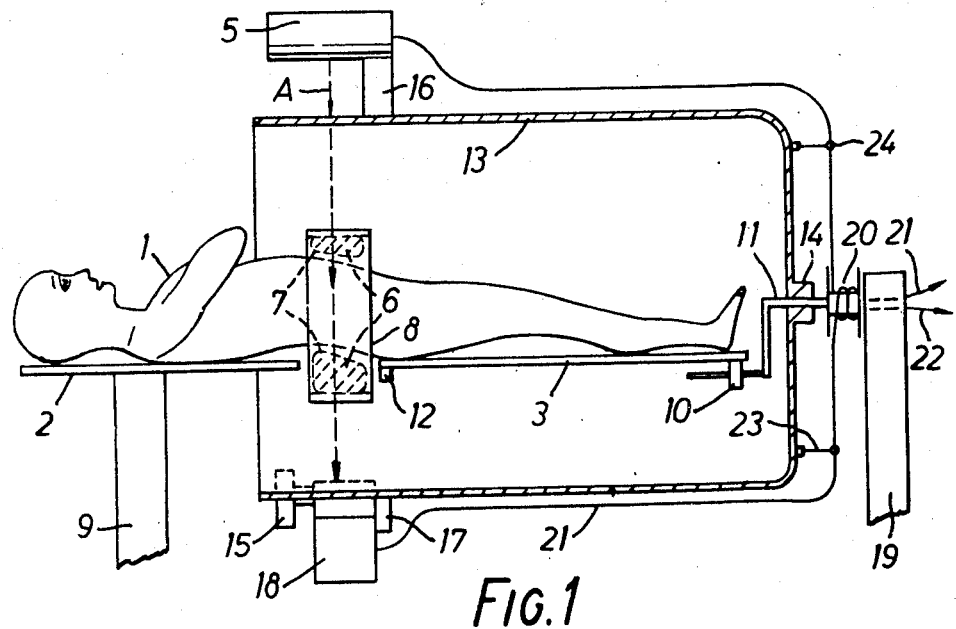
FIG. 1 shows the general layout in side elevation of an apparatus in accordance with the invention.

In FIG. 1 a patient 1 is shown lying on supporting means formed in two parts, 2 and 3 and his body is subject to examination by X-radiation indicated in broken line at 4. This radiation is generated by a source 5 and forms a fan shaped spread in a plane lying at right angles to the plane of the paper. It will be appreciated that the patient supporting means has to be sufficiently long to allow any desired section of the patient's body to be located in the plane of the X-radiation.

In the region of the exploring radiation, the body of the patient is surrounded by a liquid medium, which may be water, and which has an absorption coefficient for the radiation closely similar to that of body tissue. The liquid is shown in the figure at 6 and contained within an envelope, or bag seven. The envelope 7 is positioned within a ring like structure 8 which may be of metal such as duralumin.

The ring member 8 is held by retaining means not shown in the figure, and an important feature of this means is that it allows traverse of the ring member 8, together with the patient, along the direction of the axis of the ring, and moreover allows of displacement of this member in the plane of the exploring radiation in any direction. Thus a particular cross section of the body of the patient can be selected for examination by longitudinal traverse of the ring member 8 and the patient. The displacement possible in a direction normal to the axis of traverse permits of a local area of the cross section selected to be examined in fine detail as will be explained more fully later.

With displacement of the ring member 7 at right angles to the axis of longitudinal traverse, the parts 2 and 3 of the patient supporting means are arranged by suitable means to undergo similar displacement, and a support 9 for the part 2 is arranged to allow of this though the means is not shown in the figure. The part 3 is supported at its end remote from the ring member 8 by one or more rollers 10. Each roller 10 is carried on a bearing supported by an axle member 11, which member has an axis about which the orbiting motion of the X-ray source 5 takes place as will be made more clear. The support of the part 3 by the roller 10 allows of the displacement of the part 3 along with the ring member 8 when this is displaced laterally for the purpose of local area selection. At the other end of the part 3 from the roller 10 the part 3 is hinged at 12 to the ring member retaining means, thus allowing of vertical displacement of the member 8 for the purpose of local area selection.

Around the body of the patient when he is located in position in the apparatus there is disposed a surround or frame 13 which is cylindrical along its length having a longitudinal axis which is the axis of the axle member 11. At its end adjacent this latter member it is closed and supported by a bearing 14 which in turn is supported by the member 11. At its other end it is open to allow of positioning of the patient within it, and at this end it is supported on rollers 15 which have suitable fixed bearings. These rollers 15 are such that the surround member 13 is free to rotate on its axis, which as has been indicated is the axis about which the orbiting motion of the X-ray source 5 takes place. The source 5 is mounted on the surround member 13 by means of a support 16. Directly opposite the source 5 there is mounted on the surround member 13, by means of a support 17, a detector means 18 so as to provide radiation absorption data from the body of the patient in the plane of the radiation from the source 5.

The axle member 11 is carried by a support 19 and adjacent the support 19 and surrounding the axle member 11 is a bobbin 20. This last element is fixed to the support 19 and wound round it are cables 21 and 11, respectively carrying absorption data from the detector means 18 to the processing unit and supplying power for the X-ray source 5. With the orbiting motion of the source and detector means the cables wind on or off the bobbin 20. They are fed to the bobbin via guides 23 and 24 respectively which are carried by the surround member 13. This member may make one or more orbiting revolutions and the cables wrap or unwrap in relation to the bobbin 20 correspondingly. At the bobbin the cables are secured and thence pass to their respective connecting units, namely the data processing unit mentioned, and a power supply unit.

Figure 2:
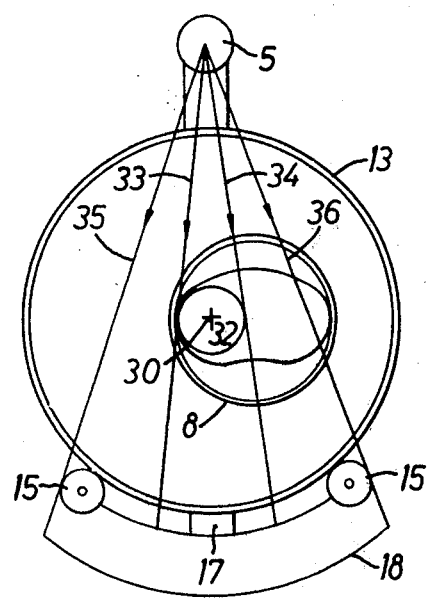
FIG. 2 illustrates the same apparatus in end elevation.

FIG. 2 as stated shows an end view of the apparatus illustrated in FIG. 2 and elements 5, 8, 13, 15, 16, 17 and 18 have the same significance as in FIG. 1. At 30 in FIG. 2 there is indicated the location of the orbiting axis and 31 shows the outline of the cross section of the patient's body in the plane of the exploring radiation. The circle 32 lying within this cross section, and centred upon the orbiting axis 30, defines a selected local area, namely the area contained within it, over which the processing unit which processes the absorption data derived from the detector means 18 operates to provide high resolution information concerning the absorption distribution of the patient's body in the examined cross section. The selection of the local area, as has been indicated earlier, is accomplished by appropriate displacement of the patient's body in a direction normal to the orbiting axis of the apparatus, the displacement illustrated in FIG. 2 being primarily a lateral one.

FIG. 2 furthermore shows particular rays 33, 34, 35 and 36 emanating from the radiation source 5. Rays 33 and 34 lie tangentially with respect to the circle 32 enclosing the selected local area, and rays 35 and 36 lie on the extreme edges of the fan of radiation from the source 5. As will be explained more fully the radiation lying between the limits set by the rays 33 and 34 is subdivided into narrow beams to provide absorption data while outside these limits the radiation is subdivided into broader beams. As will be seen from the figure, the detector means 18 extends over the whole spread of the fan of radiation from the source 5, namely from ray 35 at one extreme of the fan to ray 36 at the other extreme.

Figure 3:
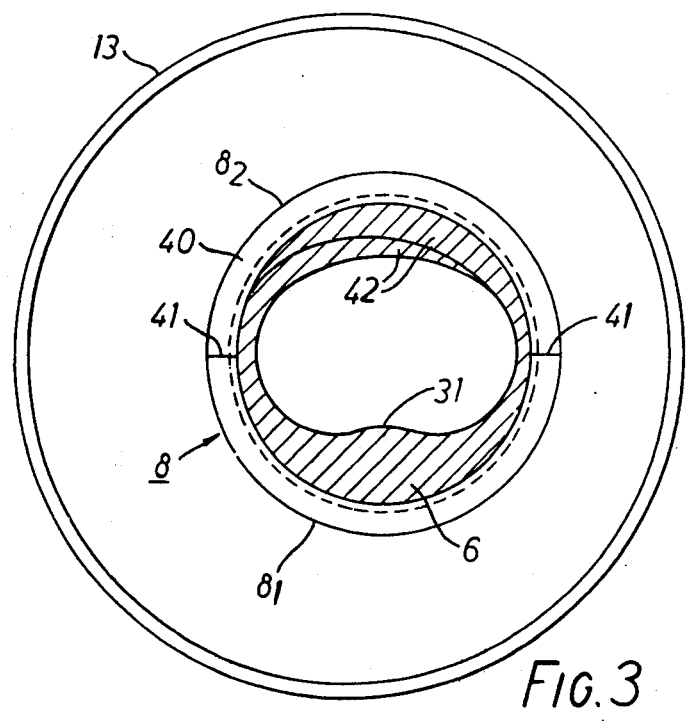
FIGS. 3 and 4 illustrate parts of the apparatus in relation to the use of a liquid medium surrounding the patient's body in the immediate vicinity of the region under examination.

Referring to FIG. 3, the ring member 8, and liquid medium 6, for positioning the patient in the apparatus is again shown in relation to the surround member 13, but in rather more detail than in FIG. 1. Thus as shown in FIG. 3 the member 8 is flanged at its ends as indicated in the figure at 40 to increase its rigidity, and split at 41 into two halves, namely a lower half $8_1$, and an upper half $8_2$, those halves being relatively located by suitable means such as pins, for example, not shown in the figure. The liquid medium 6, which as stated earlier may be water, is contained within a wrap-round form of envelope, or bag, 42, corresponding to 7 in FIG. 1. This bag is located by the cylindrical portion of the ring member 8 lying intermediate its flanged ends. Contained within the bag and ring member the patient's body is constrained to occupy some displaced position within the surround member 13 as required by the selection of the local area for examination in special detail.

Figure 4:
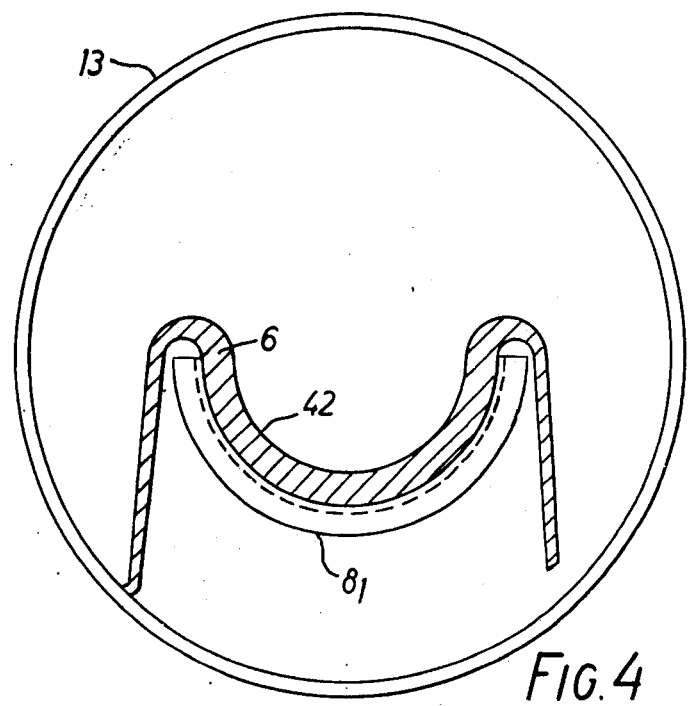

In FIG. 4 the arrangement is shown with the upper half $8_2$ of the ring member 8 removed, and the bag 42 lying unwrapped over the lower half $8_1$ of the ring member, this half being disposed in undisplaced relation with respect to the surround member 13. The arrangement shown is such as might be the case immediately prior to the entry of the patient into the apparatus. With entry, the bag 42 is wrapped round the patient in the region of required examination, the upper half of ring 8 is fitted into place and secured in position, and the bag is inflated with the liquid medium so that the medium fills all the space between the patient's body and the ring. The patient and ring together are then moved axially of the surround member 13 until the examination region is brought under the X-ray source 5, and patient and ring are then displaced normally with respect to the axis of 13, namely the orbital axis of the apparatus, for the required local area selection. A number of ring members such as 8, but of differing diameters, may be used, that member fitting most closely around the patient being chosen, so that minimum absorption of X-ray photons occurs in the liquid medium 6.

It will be realised that particularly with extreme displacement of the examined cross section in a direction away from the orbital axis of the apparatus there will be a tendency for certain rays of the fan of radiation, to be subject to large variations of overall absorption in the course of the orbital motion of the apparatus. Absorbing means, such as shaped blocks of the material known by the registered trade mark "Perspex" and indicated in FIG. 8 by reference numeral 69 are preferably provided to mitigate this effect. Other variants of the said apparatus are also described in the said co-pending patent application.

Figure 5:
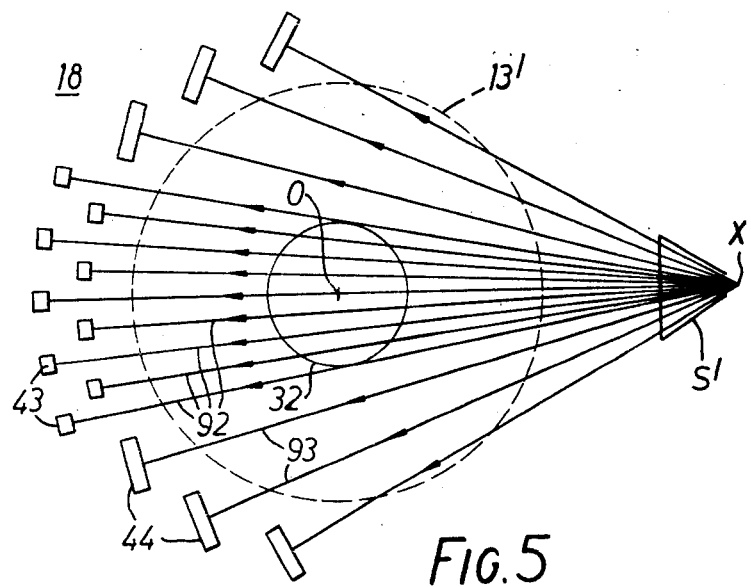
FIGS. 5 and 6 illustrate features of the detecting means used to detect the exploring radiation after its passage through the patient's body.

FIG. 5 shows the arrangement of detectors in the detector means 18 referred to in relation to FIGS. 1 and 2. This means has the object of providing the absorption data which on suitable processing, such as will be described subsequently, enables an image to be reconstructed of the cross section, of the patient's body, examined by means of the exploring radiation from a point source. In FIG. 5 the point X denotes the point source of the radiation, this point source orbiting about the axis, at O, of the apparatus. The figure shows in broken line the extreme circular 13' centred on point O, if the patient's body in any possible position. The circle 32 represents the bound of the area for which image reconstruction is effected with high resolution. The circle 32 is also centred on O and any area of the cross-section of the patient's body which it is desired to reconstruct in high resolution must necessarily be located within the area contained by 32.

In diagrammatic manner various rays are shown proceding from the point source X and these rays pass through the area within the bound 13' to fall on a multiplicity of radiation sensitive devices denoted in the figure by 43 and 44. It will be seen that in so far as the rays from X pass through the region bounded by the circle 32 they are shown as relatively many and closely spaced, whereas those rays lying more towards the extremes of the fan and not passing through the circle 32 are shown as comparatively few and widely spaced. In this respect the figure illustrates diagrammatically the principle mentioned earlier that the selected area of the cross-section of the patient's body concerning which information is required in fine detail is examined by closely spaced narrow beams whereas areas lying outside the selected area are explored by relatively broad widely spaced beams. It will be realised that to the extent that the radiation sensitive devices 43 and 44 collect photons of the radiation they each correspondingly define a beam of radiation.

Collimators, not shown, are located in front of the radiation sensitive devices to define the apertures of the devices and respective beams. The radiation sensitive devices denoted by 43 in the figure have apertures of relatively small width but are closely packed. These define many beams passing through the selected area defined by the circle 32. The remaining radiation sensitive devices 44 have apertures of relatively larger width and define broader beams. The widths of the various beams defined in the way just described will be referred to in greater detail hereinafter.

The outer beams may also be of considerably reduced intensity with the corresponding and added advantage of reduction of the dose of X-ray, to the patient. By this means, and by reconstructing the absorption pattern in fine detail only over a limited area, the reduction in dose, as compared with reconstruction of the whole area of cross-section in such detail, may be in the ration of 4 : 1.

The radiation sensitive devices 43 and 44 take the form of so-called scintillation crystals and each crystal when irradiated from the source 5 generates light which is incident upon an associated photo-multiplier. The respective photo-multipliers are not shown in FIG. 5 in the interests of simplicity, but they have the function of transforming the light output from the respective crystals into electric currents which are fed to the processing equipment for the purpose of image reconstruction. The scintillation crystals may be of sodium iodide type, such as is commonly used for scintillation purposes.

The photo-multipliers associated respectively with the scintillation crystals of the detector means 18 are relatively bulky and they present the problem of accommodating them conveniently in the apparatus.

Figure 6:
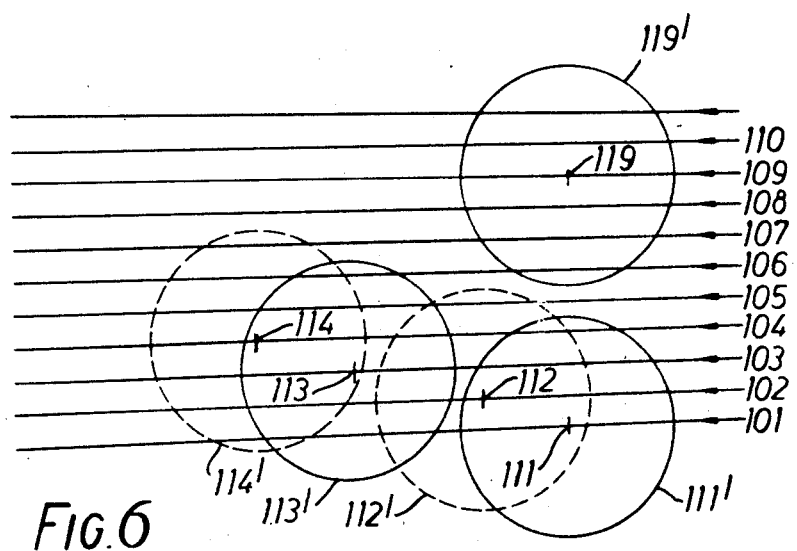

FIG. 6 shows a suitable way in which the photomultipliers may be disposed.

In this figure, which presupposes the radiation source to lie to the right, the rays 101, 102, 103 . . . are to be regarded as representative of the relatively narrow beams of FIG. 5 falling on scintillation crystals such as 43. The ray 101 may be considered as representing an extreme beam of this set of beams. The location 111 marked on it is to be taken as the location of the scintillation crystal on which the beam is incident. Centred on the location 111 there is shown the photomultiplier 111' which is excited by the scintillation of the crystal at 111. The photomultiplier 111' is shown drawn in full line and this is intended to signify that the photomultiplier lies to one particular side of the plane of the exploring beams of radiation. The adjacent beam represented by the ray 102 falls upon a corresponding scintillation crystal located at 112 and excites a photomultiplier 112'. This photomultiplier is shown drawn in broken line to indicate that it lies on the other side of the plane of the exploring beams to photomultiplier 111'. The beam represented by ray 103 falls on a scintillation crystal at 113 to excite photomultiplier 113'. This photomultiplier lies on the same side of the exploring beams as 111'. Continuing, the beam represented by ray 104 falls on a scintillation crystal located at 114 with excitation of photomultiplier 114'. This photomultiplier is disposed on the side of the beams remote from photomultiplier 111' and 113'. The pattern of this arrangement proceeds similarly for rays 105, 106, 107, 108, but with ray 109 scintillation crystal is located after the same manner as is the scintillation crystal in the case of ray 101. From this point, the cycle of disposition of the photomultipliers repeats, and continues repeating until all the rays representing the relatively narrow beams are accounted for.

Figure 7:
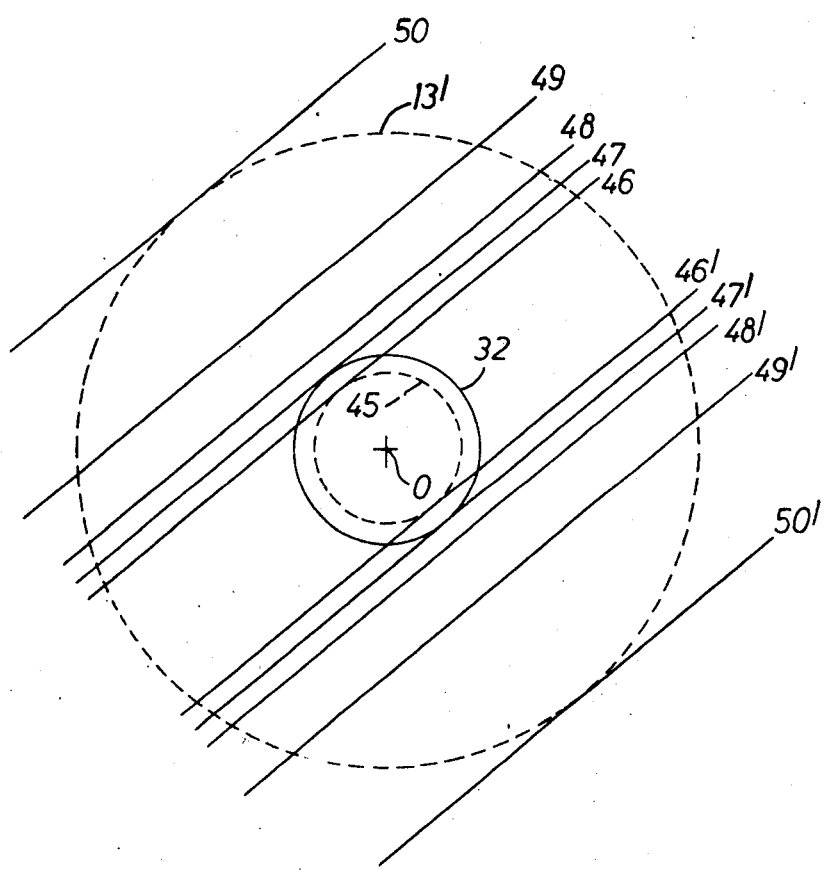
FIG. 7 is an explanatory diagram relating to the distribution of the multiplicity of radiation sensing devices used in the detecting means as described with reference to FIGS. 5 and 6.

FIG. 7 illustrates the distribution of relatively narrow and relatively broad beams across the fan of radiation emitted by the source 5. A point to be noted is that the various beams are relatively divergent, but as will be explained later, the data is assembled in sets relating to the absorption suffered by parallel beams and the data processing proceeds on the basis of parallel sets. In FIG. 7, and for this reason, the arrangement of beams is shown as if they were in fact parallel. This being effectively so, the figure illustrates the passage of a set of parallel beams through the region contained within the perimeter 13' within which the cross-section of the patient must lie.

As in FIG. 5, the point O denotes the location of the axis of orbital rotation and 32 the circle within which image reconstruction of a selected area of the cross-section of the patient's body is to be reconstructed in fine detail. Concentric with 32 and lying within 32 is the circle 45, and within this circle image reconstruction conforms to a particular degree of accuracy regardless of whatever absorbing material may be present outside of the boundary 32.

In the figure, 46 designates a boundary which is tangential to the circle 45, and 46' similarly designates a boundary diametrically opposite and tangential also to the circle 45. Between the boundaries 46 and 46' there are a total of 80 parallel exploring beams each having a mean width of 1mm in this example of the invention. The boundary 47 parallel to the boundary 46 is tangential to the circle 32 on the same side of the point O as boundary 46. In like manner boundary 47' parallel to boundary 46' is tangential to circle 32 in diametrically opposite fashion to boundary 47. Between the boundaries 46 and 47 and between rays 46' and 47' there are in each case a total of, in this example, 13 parallel beams each of mean width 1mm. Boundary 48 is drawn parallel with boundary 47 on the same side of the orbital axis O and on the other side of the axis the boundary 48' is drawn in similar relation to the boundary 47. Between each of these pairs of boundaries there is one single beam of 3mm mean width. Furthermore, boundary 49 is parallel with boundary 48 on the same side of the axis at O, while boundary 49' on the other side of the axis is disposed in identically similar relation to 48'. Between each of these pairs of boundaries there is one beam of 10mm mean width. Finally, the extreme boundary 50, parallel to the boundary 49, just touches the circle 13' on the same side of the axis at O while on the other side the boundary 50' is likewise situated in relation to boundary 49'. Between these last two pairs of boundaries there is in each case one beam of mean width 55mm. It will be understood that in referring to the beam described in relation to FIG. 7 as parallel beams, or in referred to any set of parallel beams, the parallelism is to be understood as the parallelism of one beam to another rather than that each beam in itself is strictly a parallel beam. The references to the beam width in the foregoing is the width as determined by the collimators measured along a line perpendicular to a central ray passing through the point O. The centre lines of adjacent narrow beams in the central area are moreover 2mm apart, and the gaps between them are filled in with other beams as will be explained later. In fact the effective beam width is wider than 1mm, because of spreading caused by effective presence of a "scanning aperture".

It will be appreciated that other distributions of narrow and broad beams may be utilised. Furthermore each of the broad beams may be replaced by a single narrow beam. In that case the absorption measured by such a narrow beam would be used as the absorption value for each of a number of narrow beam dispositions which would otherwise have covered the broad beam region. Such an arrangement would also give the reduction in X-ray intensity referred to above.

Figure 8:
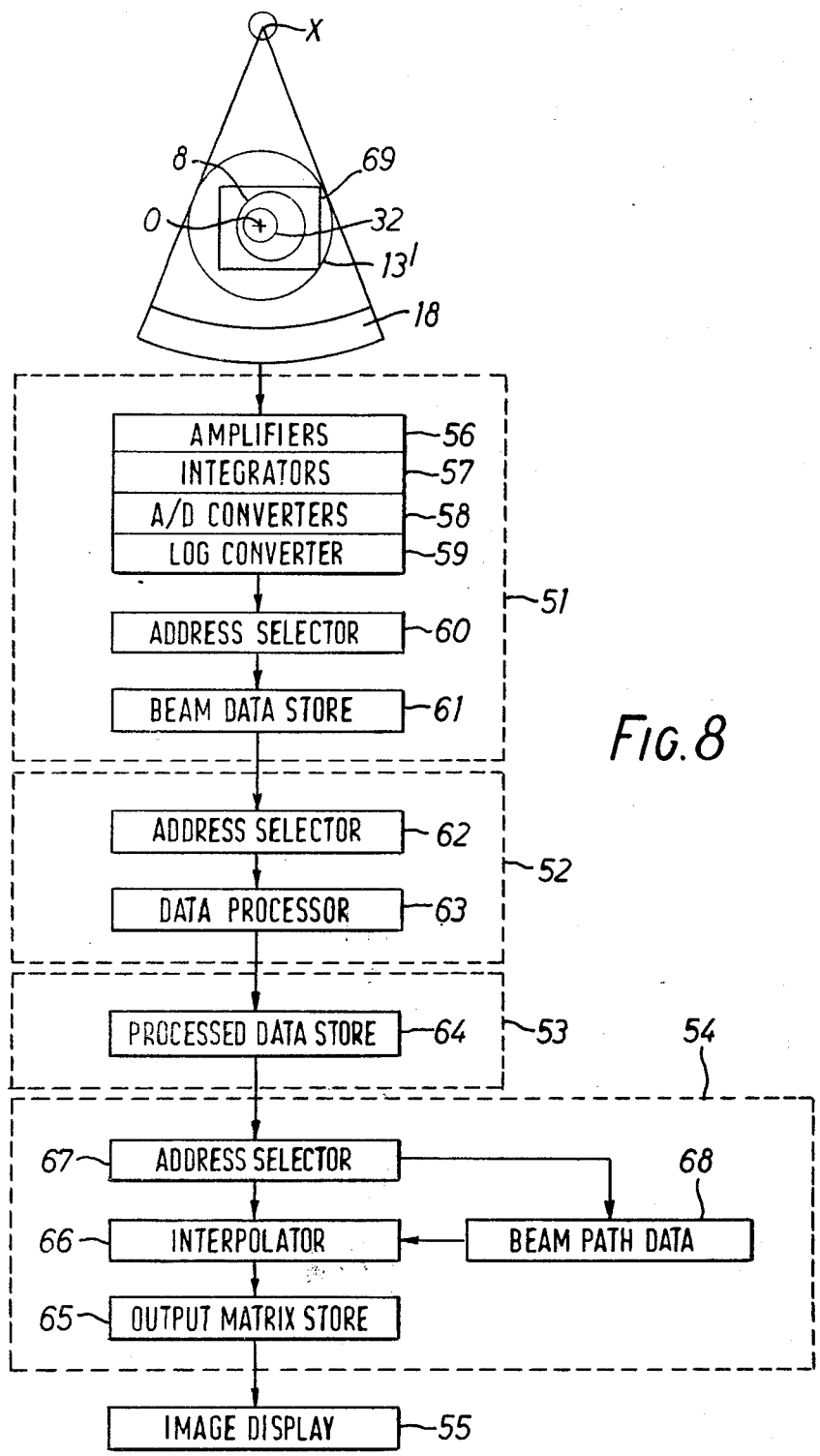
FIG. 8 shows in diagrammatic form the general layout of the entire apparatus including those parts concerned with processing of the absorption data.

FIG. 8 sets out diagrammatically the general layout of an entire apparatus of which the scanning part is illustrated in FIGS. 1 to 4.

In this figure, the point X again denotes the point of emission of X-radiation from the source 5, the point O the location of the orbital axis, the circle 32 the area of high resolution, 13' the area within which the cross-section concerned must be located, 18 the detector means providing absorption data for processing and 69 the absorbing means referred to hereinbefore but not show in the earlier figures.

The block 51 represents a store and auxiliary components for receiving and holding absorption data from the detector means 18 as it is produced in the course of the orbital motion of the apparatus. The block 51 also includes respective amplifiers 56 for the output currents from the various photomultipliers of the detector means 18 as they are received in the unit 51. The gains of the amplifiers are individually adjusted to compensate for the differing sensitivities of the various scintillation crystals of the detector means 18. The various output currents from the amplifiers are respectively integrated by Miller integrator circuits 57, the outputs of these circuits being respectively converted from analogue to digital form by converters 58 before storage occurs. If desired the gains of the amplifiers may be commonly controlled to compensate for any variations that may occur in the emission intensity of the X-ray source.

It is desired that the final image reconstruction shall represent the distribution of the absorption coefficient over the area of the cross sectional material under examination. That absorption coefficient is the absorption per unit length in the immediate vicinity of a given point of an exploring beam passing the point. To achieve the required result, it is necessary that each output signal derived from the detector means 18 shall be converted to its logarithmic form. For this purpose the unit 51 includes a log-converter 59 comprising logarithmic look-up tables according to known usage. Each signal from the integrator, after conversion to digital code is thus converted by 59 into its logarithm and is then written into the store 61 as its logarithm in digital code. The address in the store is selected by address selector 60.

With the completion of logarithmic storage in unit 51 data is drawn from such storage by the processor unit 52. The nature and operation of this unit is fully described in the aforementioned cognated patent application. The technique described therein for the processing by the unit 52 can be described as that of producing a corrected layergram. The unit withdraws data from storage in 61 in parallel sets as earlier referred to by means of address selector 62, and processes these sets simultaneously, each set being processed in a term-by-term manner in a data processor 63. As the processing of each set takes place the processed data is stored term-by-term in a processed data store 64 in unit 53, the store having different sections each for accepting the data deriving from one respective set only.

The unit 54, for accepting stored data from unit 53, includes a so-called output matrix store 65 in which the data, when all processing is complete, is held in a form in which it directly represents the distribution of absorption coefficient over the area of cross-section examined. The addresses of the store correspond to the meshes of a, for example, Cartesian meshwork, each mesh representing directly a particular elemental area of the cross-section examined, and all the meshes together extending without discontinuity so as to include all, at least, of the area of interest in the examined cross-section. At the address of each mesh there is finally stored a signal which represents, to the degree of accuracy permitted by the equipment, the absorption coefficient of the material of the body lying within the elemental area of the mesh concerned. When the storage is complete for all meshes, the image may be displayed for example by cathode ray tube or by print out, or again either in addition or as an alternative, may be transferred to magnetic tape storage. For any selected one of these purposes, or any selected combination of them, the unit 55 functions in accordance with common usage to withdraw data from the meshwork store 65, and use it for the display selected.

As a high degree of accuracy is required in the image reconstruction, interpolation is performed in the unit 54 by means of an interpolator 66 transferring the processed data stored in the respective stores 64 of unit 53 to the output matrix store 65. The interpolation is acheived by co-operation between an address selector 67 and a beam path data store 68 as described in the aforementioned cognated patent application.

In the apparatus being described the angular separation of the narrow beams, which are 1mm wide, is 2/15 of a degree, and output signals are derived from the detectors after each angular displacement of the source 5 about the centre O of 2/15 of a degree. After each increment of rotation of this magnitude, each narrow beam will assume a position which is parallel to the position which one of its neighbours occupied prior to this increment of rotation.

It is therefore possible by suitable timed selection to assemble beam absorption data signals for sets of parallel beams. Selection of this nature could produce signals corresponding to parallel sets of beams angularly separated by 2/5 of a degree. However the processing used in this example is arranged to provide such sets at ⅔° separation. This will be described in more detail hereinafter. The selection of parallel sets of beams in this manner is the subject of our co-pending patent application No. 4562/74 and was invented by G. N. Hounsfield.

The signal processing system used in conjunction with the present invention is the convolution method which is described in differing forms in the aforementioned co-pending cognated patent application. The technique essentially consists of arranging the exploring beams in groups related to zones which are concentric with a point for which an absorption value is to be calculated. These groups are chosen such that a first group passes through all such zones, a second group passes through all but the central zone, a third group passes through all but the innermost two zones and so on. The absorptions of the beams in each group are then totalled for that group and multiplied by respective zonal factors, known as "L-factors". The sum of the totals, as thus weighted, is proportional to the absorption of the material in the plane examined and at the chosed evaluation point. A plurality of such values for a suitable number of evaluation points is then used to build up the desired image.

In the aforementioned cognated application only the case of exploring beams all of which are of equal width was considered in relation to the underlying principles of processing acquired beam absorption data to yield a useful image reconstruction. The techniques outlined may be applied to the narrow-width beams described with reference to FIG. 9.

With regard to the broader beams that have been referred to, such beams are utilised for the purpose of adding in small final corrections, and procedures of great exactitude do not require to be applied to them. One method of treating them is to regard each as a contiguous set of fine beams, apportioning the broad beam absorption equally among the notional fine beams. Alternatively, as mentioned hereinbefore a single fine beam may be used to obtain an absorption value which can be allocated to each such notional beam. This single fine beam may be conveniently placed in a position which would have been central to the equivalent broad beam. The fine beam series of L-factors is then extended to include the notional fine beams. If the multiplication of absorption values by L-factors can be performed very rapidly, by for example a special form of circuit such as is described the co-pending cognated application, then this procedure may be adopted. On the other hand, with slower methods of computation, time in processing can be saved by assigning special L-factors to broad zone corresponding to broad beams.

A particular case in illustration of this technique is afforded by the situation in which the point in the cross section at which the absorption is required to be evaluated is on the axis of orbital rotation. In this event, and referring to FIG. 7, the annular zones corresponding to fine beam width extend out from the point O as far as the circle 32. The next surrounding zone is one of width equal to the distance between the bounds 47 and 48. The next further surrounding zone is one of width equal to the distance between bounds 48 and 49, and finally there is a zone, surrounding all, of width which is the distance of bound 50 from bound 49.

Considering first the innermost broad zone this may be thought of as three narrow zones concentric about the point O that continue the sequence of fine beam zones envisaged as extending as far as the circle 32. In this notional sense the fine beam sequence of L-factors is correspondingly extended. Then however rather than use these latter factors directly their average value is employed to multiply the innermost broad beam absorption, and is thus taken to be the L-factor appropriate to the first broad zone.

On the same form of procedure an L-factor is also assigned to the next surrounding broad zone, and in the same way a corresponding L-factor is determined for the final broad zone. As an example a typical value of the L-factor for the first broad zone is 0.001, while that for the next zone is 0.0006, and that for the final zone is 0.00005. For the reason that the degree of correction effected by the broad beam is small only the broad beam L-factors do not require to be determined with great precision. Moreover, with few broad beams to take into account it is not difficult to find L-factor values for broad zones by the process, if desired, of trial and error.

The situation is not quite so simple in general as in the particular case just considered, that is to say when the evaluation point is not on the orbital axis. The procedure then, which still allows overall of a useful saving in time of processing may be explained most simply by assuming the equivalent L-factor multiplication procedure that is adopted in practice for convenience, and which will be referred to again in more detail. As it has been explained thus far the L-factor multiplication procedure is one in which beam absorptions are summed in zones and the absorption sums each multiplied by the corresponding L-factor, all sums so weighted then being added. It is an equivalent procedure to multiply out the L-factor series not on the zonal basis as just stated, but taking one parallel set of absorption data at a time to multiply out the L-factor series with the absorption values of the set in an otherwise identical manner. It is necessary then to store the multiplication products in intermediate store. For the present, however, it is sufficient to consider that in proceeding with a parallel set there will be linear intervals corresponding to the zonal intervals and equal to the zonal widths, with respect to which linear intervals the L-factors are now distributed rather than with respect to zones. With the introduction of broad beam L-factors, these factors will be associated with broad beam intervals, just as fine beam L-factors will be associated with fine beam intervals.

It will be evident that in the multiplication with a parallel set it can happen that a fine beam series of intervals overlies entirely a broad beam. In this circumstance the broad beam absorption datum is resolved into a sequence of notional fine beam absorption data of equal value totalling the broad beam datum. If the fine beam series only partially overlies a broad beam then the broad beam is resolved only to this partial extent with respect to the fine beam series for fine beam multiplication leaving over a residual and adjacent notional broad beam. The absorption value to be associated with this notional broad beam is appropriately used in broad beam L-factor multiplication. For example the beam absorption value may be added to another constructed value deriving from an adjacent broad beam, the sum value being multiplied by a corresponding broad beam L-factor. Where a broad beam interval falls over fine beams, the fine beam data are summed to construct the absorption appropriate to a notional broad beam of the width of the interval, and this absorption is then multiplied by the L-factor for the interval. On these lines the absorption can be evaluated with respect to any point in the examined cross-section, and with a saving in processing time as compared with processing of purely fine beam type.

As will be realised whether broad beam L-factors are made use of in the processing, or not, the utilisation of broad beams in themselves is valuable for the reason of the saving they permit in the number of scintillation crystals and corresponding photo-mulitpliers.

In regard to the scheme of beams considered with respect to FIG. 7 it is to be noted that, apart from their parallelism with one another, the beams have implicity been treated as though they were of uniform width. However, in the apparatus of FIGS. 1 and 2, the beams defined by the detectors are not of this character, being narrower on one side of the explored field and wider on the other. The effect of this disparity is minimised in the apparatus described by not restricting the orbital motion to the theoretical range of 180°, but by allowing it to continue for 360° so that for every beam disposition of the first 180° of scan there is a second which is identical except for the fact that the direction of passage of radiation is reversed, and with it the sense of the disparity. The average of the two beam absorptions is then taken to produce data corresponding to a beam of virtually uniform width.

Figure 9:
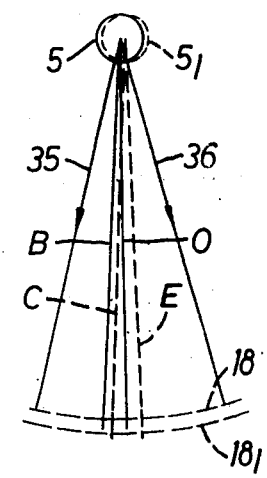
FIG. 9 illustrates a feature of the apparatus.

A further extension of the orbital motion is also used to reduce the number of scintillation crystals and corresponding photo-multipliers used in connection with the large number of narrow-width beams. Thus the number of pairs of these crystals and photo-multipliers is halved by leaving a gap of one beam width between each successive pair, and the gaps consequently left in the group of narrow-width beams are made good by a lateral displacement of the X-ray source and detector means to the extent of one narrow beam. A further orbital rotation of 360° then provides the missing information. This is illustrated in FIG. 9 which shows at 5 and 18 the positions of the X-ray source and the collimators for the scintillators during a first of two orbital rotations. This figure also shows at $5_1$ and $18_1$ the positions of the X-ray source and the collimators during the second of the two orbital rotations, showing by dotted lines the result of displacement of the beams to fill the gap between the beams indicated by the full lines.

This technique may however be dispensed with by using close packing of photo-multipliers and crystal or by using multi channel devices. Conversely the technique can be extended to make good the omission of further crystals and photo-multipliers. A three revolution method may for example be employed. However, if the apparatus is to be used for examining the body of a patient in regions where the breathing of the patient can cause undesired body movement in the cross-section of examination, unless the patient temporarily withholds his breathing, it is desirable that the time of orbiting should be brief. The number of possible revolutions of orbiting thus tends to be strictly limited. The technique shown in FIG. 9 forms part of the subject matter of our co-pending U.S. patent application Ser. No. 489,084 filed July 17, 1974 now U.S. Pat. No. 3,934,142.

Having decided upon the use of a particular series of L-factors and assuming the acquired beam absorption available in logarithmic form as earlier described, and moreover available in the form of parallel sets, the processing to be performed by the unit 131 of FIG. 8 may be accomplished by means of an appropriately programmed computer or the special circuits described in the aforementioned cognated patent application.

As previously indicated, and in relation to the fine exploring beams, the angular interval between the equally angularly spaced parallel sets of data is chosen to be ⅔°. Considering detectors spaced at intervals of ⅔° about the orbital axis; it will be evident that the readings of successive detectors will relate to a parallel set if they are taken after successive movements of ⅔°. Another parallel set may be started, from the first detector, after the first movement of ⅔°, this second set being inclined at ⅔° to the first set and so on, yielding sets at all the required angles. With the relatively narrow beam widths employed in the apparatus, four detectors are however interposed between each pair disposed at ⅔° spacing, the interposition being such as to give a 2/15° interval between detectors. Consider now FIG. 10, which illustrates the group of components denoted by unit 51 in FIG. 8 in more detail. All detectors included in means 18 are regarded as falling into one or other of five different categories. Category 1 may be regarded as that of the initial sequence of detectors between which the added four detectors are interposed. Category 1 detectors are thus the first of successive groups of five detectors. Detectors of category 2 are the second of these groups; category 3 the third, and so on. The outputs of the detectors of different categories are then sampled at different times according to their category. Detectors of category 2 are sampled at time T later than those of category 1, while those of category 3 are sampled at time 2T later, and so on, the sampling cycle occupying time 5T, this time being the duration of scanning of the orbital motion over ⅔°.

It has been seen that, using the data from those detectors now classed as detectors of category 1, parallel sets of data can be constructed with an angular interval of ⅔°. In any set so constructed the data corresponds to beams spaced apart by intervals of extent such as to accommodate the spread of four intervening beams at the spacing of fine beams. Data corresponding to the locations of such intervening beams is derived by means of the sampling of the outputs of the detectors of categories 2, 3, 4 and 5 so as to provide full sets.

In general, beams of a fan having an angular spacing of $\alpha$ may be combined in $n$ categories to provide parallel sets at $n\alpha$ angular separation. However each such set will have $n$ times the number of beams provided, at the same separation, by a fan of beams of spacing $n\alpha$. In the case described hereinbefore $n$ is given as 1 and $\alpha$ is 2/15°. Therefore $n\alpha$ is also 2/15°. In the example relating to FIG. 10, $n = 5$ and $n\alpha$ is therefore ⅔°.

The duration of sampling, at any time of sampling detector outputs, is such as to correspond to the fine beam spacing, allowing for 'aperture effect' to spread the effective radiation density distribution across the beam so that the overall effective spread of the beam is twice the spacing of beams of a finally derived parallel set. Sampling is effected by causing the Miller integrators 52 earlier mentioned to start and cease integrating at appropriate times, and deriving their integrated outputs. The Miller integrators are thus used in their known role of analogue stores in which they sample and hold, thereafter to be reset so as to be available for further sampling in the same manner. The derived parallel sets of data as they are derived are stored in respective stores so as to be directly available for convolution.

In FIG. 10 output conductors 70 proceding from the detector means 18 carry the outputs of those detectors giving narrow-beam absorption information, one conductor being associated with each such detector. The conductors 70 are shown separated out according to the respective detector categories 1, 2, 3, 4, 5. As so classified the conductors proceed into the initial processing and storage unit 51.

The outputs of the broad beam detectors correspond respectively to the notional fine beams into which the broad exploring beams may be regarded as resolved. For example a broad beam of 10mm width is regarded as resolved into 10 notional fine beams. In principle the detector sensing the absorption suffered by the broad beam thus feeds outputs into 10 separate fine beam channels, a separate output conductor applying signals to each channel. Since however each such signal must be the same, on the grounds that there is no reason to apportion the detector output other than equally, in practice each broad beam detector feeds one output conductor only and one corresponding channel. On this understanding the operation of these channels will become clear with the further description of the equipment in relation to the outputs of the detectors giving information concerning the absorption of the fine exploring beams. For simplicity therefore detector output conductors relative to the broad exploring beams are not shown in FIG. 10, and for the same reason only one typical fine exploring beam channel is illustrated in the figure. This corresponds to the typical fine beam detector output conductor 70.

After initial processing, immediately to be described, the data is distributed to the sections 1, 2, 3, ... $n$ of store 61 (FIG. 10) to which the data deriving from all other conductors is correspondingly communicated, so that in each store there is held the data of one parallel set, one store being used for each set.

Considering the typical conductor, designated $70_k$ in the figure, the currents carried by the conductor are applied to the input of the gain controlled amplified $56_k$. The gain of this amplifier, as indicated earlier, is adjustable so that the relative sensitivities of the various detectors may be compensated and so that variations in the emission from the X-ray source may also be compensated. The gain control may also provide means, if desired, for compensating for drift in the relative sensitivities in the course of scanning. The various amplifiers such as $56_k$ are controlled in gain from gain control unit 71.

The output of the amplifier $56_k$ is fed to the analogue store $57_k$ which as stated earlier takes the known form of Miller integrator in sample-and-hold form. Sampling by all such circuits as $56_k$ is under the timing control of timing unit 72, which also controls the time of read out and of reset of these circuits. The read out from circuit $57_k$ is converted from analogue to digital form by the circuit $58_k$ and fed to distributor circuit $60_k$ which communicates with the various sections 1, 2, 3, ... $n$ of store 61. In the event that all the sampled data deriving from the various detectors related to parallel exploring beams, which is not in fact the case, since the exploring beams have the divergence of the radiation fan, all the distributors of which $60_k$ is typical would distribute at any one time to one store section only, corresponding to one particular angle of the orbiting scan. This store would then be completely filled at this time, disregarding for simplicity the developments described to take account of the non-parallelism of individual exploring beams, and to reduce the number of detectors employed by a factor of two. These measures as earlier noted lead to a two revolution scan rather than one of 180/20, the latter being all that is necessary in principle. However, no store section is filled in one single filling procedure even if the measures adopted reduce the apparatus to one of a simple 180° scan. Rather, contributions to a given parallel set are made over a range of sampling times in the way enunciated from a range of different detectors. Following such a programme of timing the distributor circuits such as $60_k$ contribute to the parallel set storage under the control of unit 72.

The parallel set data so set up in the store sections 1, 2, 3, ... n is available to be passed to the convolution processing unit after logarithmic conversion. To accomplish this conversion and as data is established in the addresses of the parallel set stores it is fed to the logarithmic converter unit 59 to be written back into the same address from which it was withdrawn, but in logarithmic form. This is performed under the timing control of the unit 72. It is to be noted that in the form of apparatus described every address receives two contributions, one corresponding to one direction of transmission of the relevant beam, and one to the beam in 180°relation of scan. The data at an address is not complete until both such contributions have been made and logarithmic conversion cannot be effected until that time.

It will be understood that the present invention may be applied to any scanning arrangement suitable for apparatus of the type described in the aforementioned specification and applications, in particular a linear scan superimposed as an orbital scan. As a further example, considering the technique described for selecting sets of parallel beams from a larger set at a variety of angular dispositions, other methods are known for assembling such a larger set. In one method a fan shaped distribution of beams is given a linear scan and further orbited to repeat that scan at a variety of angles. However it has been found that extreme positions of the linear scan may not provide enough individual beams to complete all of the parallel sets. In such cases, according to the invention, absorption information required for a disposition for which a beam is missing may be supplied by any other beam lying sufficiently near to the required disposition.

Furthermore the invention may be combined with any suitable signal processing system.

What I claim is:

1. Apparatus for examining a body by means of penetrating radiation, such as X- or γ- radiation, comprising a radiation source projecting radiation in a plane, a plurality of detectors in said plane spaced from said source to provide space for locating the body between the source and detectors so that a plane section of the body is irradiated by said radiation, the lateral extent of the radiation being sufficient to irradiate a substantial area of said plane section, said plurality of detectors including collimators and being laterally spaced to detect radiation along different beams within the lateral extent of said radiation, a rotatable support on which the source and detectors are mounted to rotate, around the body, about a common axis normal to the said plane and the lateral spacing of the centrelines of the beams being non-uniform so that the centrelines of beams passing through a selected portion of said substantial area are relatively more closely spaced than the centrelines of beams which do not pass through the selected portion.

2. An apparatus according to claim 1 wherein said source is arranged to scan linearly in said plane to irradiate the body along some of the beams, and to rotate about the body so as to irradiate the body along others of said beams.

3. An apparatus according to claim 1 wherein said detectors each comprise a scintillator crystal coupled to a photomultiplier tube.

4. An apparatus according to claim 3 wherein said photomultiplier tubes are arranged in staggered formation to accommodate the magnitude of their dimensions said plane.

5. An apparatus according to claim 4 wherein some of said photomultiplier tubes are arranged on one side of said plane and others are arranged on the other side of said plane.

6. An apparatus according to claim 1 wherein said collimators define detector apertures whose widths are a non uniform function of beam position so that the widths of the beams are a non uniform function of beam position.

7. An apparatus according to claim 6 wherein the apertures associated with detectors receiving radiation in a central part of the lateral extent of the radiation are relatively narrow to define narrow beams of radiation and the apertures associated with the remaining detectors towards the extremes of the said lateral extent are relatively wide to define wide beams of radiation.

8. An apparatus according to claim 6 wherein the said source provides a planar, fan-shaped spread of radiation and the detectors are disposed at different angular positions in the fan, those detectors disposed toward the centre of the fan having relatively narrow apertures compared with those disposed to the extremes of the fan.

9. An apparatus according to claim 1 wherein the said collimators define detector apertures of substantially equal dimension to define beams of substantially equal width.

10. An apparatus according to claim 9 wherein those detectors disposed towards the extremes of the said lateral extent of the radiation are relatively more widely spaced than those disposed towards the centre.

11. An apparatus according to claim 9 wherein the said source provides a planar, fan-shaped spread of radiation and the detectors are disposed at different angular positions in the fan, those detectors disposed towards the extremes of the fan being at relatively greater angular spacing than those disposed towards the centre of the fan.

12. A method of examining a selected area of a planar section of a body by means of penetrating radiation, such as X- or γ- radiation, including the steps of,
   a. projecting the radiation in the plane of the said section,
   b. defining a plurality of beams of the said radiation lying in the said plane in such a way that the centrelines of beams passing through the said selected area are relatively more closely spaced that the centrelines of beams which do not pass through the selected area,
   c. determining the absorption suffered by the radiation, after passage through the body, along the said beams, and
   d. repeating the said determination of absorption for further pluralities of such beams at different angular positions in the said plane,
the arrangement being such that the determinations of absorption for the said beams not passing through the selected area can be used to correct for the effects, on the beams passing through the selected area, of absorption of radiation by the remaining parts of the said section.

13. A method according to claim 12 in which the body is moved laterally relative to the said beams of radiation to examine a different selected area of the said section.

* * * * *

UNITED STATES PATENT OFFICE
CERTIFICATE OF CORRECTION

Patent No. 3,973,128     Dated August 3, 1976

Inventor(s) Christopher Archibald Gordon LeMay

It is certified that error appears in the above-identified patent and that said Letters Patent are hereby corrected as shown below:

Column 1, line 68 and Column 2, line 1, "Cognated Application", each occurrence, to read -- U. S. Patent --. Column 9, line 39, and Column 12, line 57, "cognated patent application", each occurrence, to read -- U. S. Patent --. Column 9, line 58, after "application" insert -- Serial No. 544,799 filed January 28, 1975 which corresponds to British application --. Column 9, line 63, "co-pending cognated patent application" to read -- U. S. Patent --. Column 10, line 11, "cognated application" to read -- U. S. Patent --. Column 14, line 59, "180/20" to read -- 180 degrees --. Column 15, line 21, "specification" to read -- specifications --. Column 9, line 57, "our" should be deleted.

Signed and Sealed this

Twenty-second Day of March 1977

[SEAL]

Attest:

RUTH C. MASON
*Attesting Officer*

C. MARSHALL DANN
*Commissioner of Patents and Trademarks*